(12) United States Patent
Khazaka et al.

(10) Patent No.: US 11,147,851 B2
(45) Date of Patent: Oct. 19, 2021

(54) METHOD OF FABRICATING AN ELECTRONIC POWER MODULE BY ADDITIVE MANUFACTURING, AND ASSOCIATED SUBSTRATE AND MODULE

(71) Applicant: SAFRAN, Paris (FR)

(72) Inventors: Rabih Khazaka, Moissy-Cramayel (FR); Stéphane Azzopardi, Moissy-Cramayel (FR); Donatien Henri Edouard Martineau, Moissy-Cramayel (FR)

(73) Assignee: SAFRAN, Paris (FR)

( * ) Notice: Subject to any disclaimer, the term of this patent is extended or adjusted under 35 U.S.C. 154(b) by 0 days.

(21) Appl. No.: 16/478,326

(22) PCT Filed: Jan. 5, 2018

(86) PCT No.: PCT/FR2018/050024
§ 371 (c)(1),
(2) Date: Jul. 16, 2019

(87) PCT Pub. No.: WO2018/134495
PCT Pub. Date: Jul. 26, 2018

(65) Prior Publication Data
US 2019/0358285 A1  Nov. 28, 2019

(30) Foreign Application Priority Data
Jan. 18, 2017 (FR) ...................... 1750381

(51) Int. Cl.
*H01L 23/495* (2006.01)
*A61K 38/01* (2006.01)
*A61K 31/202* (2006.01)
*A61K 35/741* (2015.01)
(Continued)

(52) U.S. Cl.
CPC ............ *A61K 38/018* (2013.01); *A23L 33/12* (2016.08); *A23L 33/125* (2016.08); *A23L 33/18* (2016.08);
(Continued)

(58) Field of Classification Search
CPC .................... H01L 23/49513; H01L 23/49568
See application file for complete search history.

(56) References Cited

U.S. PATENT DOCUMENTS 5,561,321 A * 10/1996 Hirano .................. C04B 35/584
257/700
2003/0201532 A1* 10/2003 Riedl ...................... H01L 24/29
257/734
(Continued)

FOREIGN PATENT DOCUMENTS

DE  10 2014 203309 A1  8/2015
EP  2 991 105 A1  3/2016
(Continued)

OTHER PUBLICATIONS

International Search Report as issued in International Patent Application No. PCT/FR2018/050024, dated Mar. 26, 2018.

*Primary Examiner* — Shahed Ahmed
*Assistant Examiner* — Khatib A Rahman
(74) *Attorney, Agent, or Firm* — Pillsbury Winthrop Shaw Pittman LLP

(57) ABSTRACT

A method of fabricating an electronic power module by additive manufacturing, the electronic module including a substrate having an electrically insulating plate presenting opposite first and second faces, with a first metal layer arranged directly on the first face of the insulating plate, and a second metal layer arranged directly on the second face of the insulating plate. At least one of the metal layers is made by a step of depositing a thin layer of copper and a step of annealing the metal layer, and the method further includes a
(Continued)

step of forming at least one thermomechanical transition layer on at least one of the first and second metal layers, the at least one thermomechanical transition layer including a material presenting a coefficient of thermal expansion that is less than that of the metal of the metal layer.

5 Claims, 3 Drawing Sheets

(51) Int. Cl.
| | |
|---|---|
| *A61K 31/716* | (2006.01) |
| *A61K 31/702* | (2006.01) |
| *A23L 33/18* | (2016.01) |
| *A23L 33/125* | (2016.01) |
| *A23L 33/19* | (2016.01) |
| *A23L 33/12* | (2016.01) |
| *A61K 45/06* | (2006.01) |

(52) U.S. Cl.
CPC ............ *A23L 33/19* (2016.08); *A61K 31/202* (2013.01); *A61K 31/702* (2013.01); *A61K 31/716* (2013.01); *A61K 35/741* (2013.01); *A61K 45/06* (2013.01); *H01L 23/49513* (2013.01); *H01L 23/49568* (2013.01); *A23V 2002/00* (2013.01)

(56) References Cited

U.S. PATENT DOCUMENTS

| | | |
|---|---|---|
| 2005/0045358 A1* | 3/2005 | Arnold ................ H05K 9/0024 174/51 |
| 2005/0214518 A1* | 9/2005 | Nagase ............... H01L 23/3735 428/210 |
| 2010/0148326 A1* | 6/2010 | Mohammad ...... H01L 23/49513 257/666 |
| 2011/0061906 A1* | 3/2011 | Cho ..................... H05K 1/0271 174/257 |
| 2014/0076613 A1* | 3/2014 | Mahler ................. H01L 23/293 174/251 |
| 2015/0228616 A1* | 8/2015 | Palm ................ H01L 23/49541 257/676 |
| 2016/0325384 A1* | 11/2016 | Liu ........................ H01L 24/16 |
| 2017/0011991 A1* | 1/2017 | Khazaka ........... H01L 23/49568 |
| 2017/0092596 A1* | 3/2017 | Yoshihara ......... H01L 23/49582 |
| 2017/0186674 A1* | 6/2017 | Luan ................... H01L 23/4334 |
| 2018/0358318 A1* | 12/2018 | Shearer ............. B23K 35/3046 |

FOREIGN PATENT DOCUMENTS

| | | |
|---|---|---|
| JP | H06-24880 A | 2/1994 |
| JP | 2007-096032 A | 4/2007 |

* cited by examiner

METHOD OF FABRICATING AN ELECTRONIC POWER MODULE BY ADDITIVE MANUFACTURING, AND ASSOCIATED SUBSTRATE AND MODULE

CROSS-REFERENCE TO RELATED APPLICATIONS

This application is the U.S. National Stage of PCT/FR2018/050024, filed Jan. 5, 2018, which in turn claims priority to French patent application number 1750381 filed Jan. 18, 2017. The content of these applications are incorporated herein by reference in their entireties.

BACKGROUND OF THE INVENTION

The invention relates to fabricating a substrate and an electronic power module.

The present invention finds a particular application in the field of aviation where thermal stresses can be severe.

Electronic power modules are included in the converters needed for electrifying propulsion and non-propulsion systems on board aircraft in order to convert electricity from the main network (115 volts alternating current (V AC), 230 V AC, 540 V direct current (DC) . . . ) into various forms (AC/DC, DC/AC, AC/AC, and DC/DC).

FIG. 1 shows an example of an electronic power module 1 known in the prior art.

The electronic power module 1 is made up of a substrate 2 comprising an electrically insulating layer 2a made of ceramic material that is arranged between two metal layers 2b and 2c. The two metal layers are assembled to the electrically insulating layer 2a by various techniques, e.g. those known as active metal brazing (AMB), as direct bonded copper (DBC), or indeed as direct bonded aluminum (DBA).

The top metal layer 2b of the substrate 2 forms a power circuit on which semiconductor power components 3 are assembled. As shown in FIG. 1, the electronic power module 1 includes an electrical and/or mechanical interconnection joint 4 and 14 whereby the semiconductor power components 3 and the connections 11 are assembled on the power circuit 2b. As a result of their imperfections, the semiconductor power components 3 are the seats of Joule effect losses and they thus constitute a major source of heat.

The semiconductor power components 3 are subsequently interconnected electrically and with the connections 11 by means of wiring. A package 12, generally made of polymer, is then adhesively bonded by means of an adhesive joint 13 on the substrate 2 or on a metal baseplate 5 on which the substrate 2 is arranged. The package 12 is then filled with an encapsulating compound 15, such as a gel or epoxy, so as to provide the power components 3 and the wiring 10 with mechanical and electrical protection.

The bottom metal layer 2c of the substrate 2 is fitted on the metal baseplate 5, which serves to spread the heat flux and provides a thermal connection with a metal heat dissipater 6. As shown in FIG. 1, the electronic power module 1 includes an electrical and/or mechanical interconnection joint 7 securing the bottom metal layer 2c of the substrate 2 to the baseplate 5.

The baseplate 5 is itself secured to the metal heat dissipater 6 by means of a layer 8 of thermal interface material, such as a thermal grease, or an elastomer film, or else change-of-phase materials. The layer 8 of thermal interface material serves to reduce the thermal contact resistance between the baseplate 5 and the heat dissipater 6 in order to discharge the heat flux better. The heat dissipater 6 has fins 9 for reducing its thermal resistance as much as possible, the fins 9 having a cooling fluid passing between them, e.g. air.

Such an electronic power module 1 nevertheless presents several drawbacks.

The electrically insulating layer 2a of the substrate 2 and the module 8 of thermal interface material are layers presenting high thermal resistance and thus poor heat conduction. They thus limit dissipation of the heat generated within the semiconductor power components 3 towards the heat dissipater 6 and the cooling fluid. Furthermore, the layer 8 of thermal interface material gives rise to thermal resistance that is not uniform, and that depends on the positioning of the semiconductor power components 3 on the power circuit, in particular if the circuit presents any planeness defect. The multiplicity of layers 2a, 2b, 2c, 4, 5, 7, and 8 between the semiconductor power components 3 and the heat dissipater 6 also contributes to this high thermal resistance. Cooling of the electronic power module 1 is thus limited, and the electronic power module 1 is not suitable for high temperature applications, i.e. for ambient temperatures higher than or equal to 175° C. as a result of the presence of organic materials (thermal interface material, the encapsulating compound, the adhesive joint, and the package), which generally degrade quickly above 175° C. It should be observed that wide-band gap semiconductor components (SiC, GaN, . . . ) can operate beyond the conventional limits for Si components (175° C.), and in order to take advantage of the possibility of operating at high temperature, all of the elements making up the electronic power module need to be capable of operating reliably at high temperature.

Furthermore, solutions for assembling the various layers 2a, 2b, 2c, and 5 having mutually different coefficients of thermal expansion make the electronic power module 1 sensitive to the phenomenon of thermal fatigue, thereby limiting the reliability of the electronic power module 1. By way of example, these solutions may lead to cracking in the electrically insulating layer 2a of the substrate 2 and/or in the electrical interconnection joints 4, 7.

Furthermore, the etching performed on the top metal layer 2b of the substrate 2 gives rise to asymmetry relative to the bottom metal layer 2c about the electrically insulating layer 2a. When temperature rises, e.g. while the semiconductor power components 3 are being assembled on the substrate 2 or while the substrate 2 is being assembled on the baseplate 5 or while the electronic power module 1 is in operation, this has the effect of giving rise to thermomechanical stresses in the substrate 2, leading to it deforming. This deformation is referred to as flexing and corresponds to the substrate 2 curving.

Such flexing of the substrate 2 creates a gap that can be filled in by the layer 8 of thermal interface material. Nevertheless, as explained above, this layer 8 limits thermal dissipation between the semiconductor power components 3 and the heat dissipater 6 and gives rise to non-uniform thermal resistance that depends on the positioning of the semiconductor power components 3 on the power circuit. It is therefore not possible to compensate for the flexing of the substrate 2 by increasing the thickness of the layer 8 of thermal interface material without further degrading heat dissipation within the electronic power module 1.

OBJECT AND SUMMARY OF THE INVENTION

The invention seeks to mitigate the drawbacks of the above-mentioned electronic power modules.

The invention provides a method of fabricating an electronic power module by additive manufacturing, the electronic module comprising a substrate having an insulating plate, such as a ceramic plate, presenting opposite first and second faces, with a first metal layer arranged directly on the first face of the insulating plate, and a second metal layer arranged directly on the second face of the insulating plate.

According to a general characteristic of the invention, at least one of the metal layers is made by a step of depositing a thin layer of metal and a step of annealing the metal layer, generally at a temperature of about 700° C., and the method further comprises a step of forming at least one thermomechanical transition layer on at least one of the first and second metal layers, said at least one thermomechanical transition layer comprising a material presenting a coefficient of thermal expansion (CTE) that is less than the CTE of copper.

The step of depositing a thin layer of metal may comprise deposition by silkscreen or deposition of a thin metal layer using a paste or an ink in techniques known as direct wiring processes, e.g.: inkjet processes, extrusion based processes, aerosol based processes.

Because the thermomechanical transition layer of the substrate of the invention presents a CTE that is smaller than that of the metal layer, it serves to increase the thermomechanical reliability of the substrate compared with a direct bonded copper (DBC) substrate, and it serves to limit problems associated with substrates curving, as observed with ceramic substrates (DBC and AMB).

The method of fabrication using additive manufacturing for each step of forming a new layer of the substrate enables the method to avoid any loss of material during fabrication of the electronic power module as a result of the layers being deposited and melted selectively.

Additive manufacturing (AM), also known as three-dimensional (3D) printing, is a technique that makes it possible to make objects by adding successive layers. A power source delivers energy to well-defined locations of the powder that has been deposited as a layer that is thin (typically <100 micrometers (μm) thick) for the purpose of agglomerating it. Depositing successive layers and agglomerating them selectively thus makes it possible to build up a dense material with a well-defined shape. The ability to select which portion is agglomerated thus enables the object to be given directly a desired shape even if that shape is complex. This also serves to limit losses of material, which can be extremely desirable for materials that are expensive and rare.

Specifically, in a conventional prior art substrate, the layers of copper Cu on the top and bottom faces cover the surfaces of the ceramic completely and they are applied directly onto the ceramic by using DBC technology or by using AMB brazing technology. Thereafter, an etching step serves to remove copper Cu locally from the top face and to make tracks that are not electrically interconnected and that serve to provide an electric circuit.

In a first aspect of the method, said at least one thermomechanical transition layer may be deposited by depositing a powder bed of material or by spraying powder material, the deposited powder then being set by scanning with a heat power source in an inert atmosphere.

Typically, in prior art substrates, the thickness of the ceramic lies in the range 300 μm to 1000 μm, and the thickness of the copper lies in the range 200 μm to 500 μm. However it has been shown that the greater the thickness of the copper, the lower the reliability of the substrate during thermal cycles that lead to high levels of thermomechanical stresses.

The additive manufacturing used by the method of the invention makes it possible to make and use layers of copper that are thin, i.e. less than 100 μm thick, and more particularly of thickness lying in the range 20 μm to 50 μm, thereby providing better reliability. In addition, laying up a plurality of thermomechanical transition layers made of materials other than copper serves to increase the thickness of the tracks and thus to increase the current that those tracks can convey without limiting the reliability of the substrates.

The use of metals in additive manufacturing generally requires a power source suitable for delivering the necessary power, e.g. lying in the range 100 watts (W) to 1 kilowatt (kW), in order to melt or sinter the metal powder deposited during the additive manufacturing process in the form of a powder bed or by localized spraying of powder. The power source (laser beam or electron beam) targets zones where it is desirable to have dense material in order to obtain, on each pass, a layer that is densified and set.

The typical thickness of a deposited layer may lie in the range 20 μm to 150 μm. A new layer is then deposited and set by scanning the zone for setting with the power source. The succession of steps of depositing layers and then densifying them serves to obtain the object with the desired shape.

In a second aspect of the method, the CTEs of the materials used for the thermomechanical transition layers lie in the range 3 parts per million per degree Celcius (ppm/° C.) to 17 ppm/° C.

The thermomechanical transition layers thus present CTEs lying between the CTE of the metal layer and the CTE of the semiconductor power components that are to be mounted on the electronic power module.

In a third aspect of the method, the substrate comprises, on at least one of the first and second faces of the insulating plate, a stack of a metal layer and a plurality of thermomechanical transition layers, with said at least one stack presenting a gradient in its CTE.

During thermal cycling, this variation of CTE between the copper and the semiconductor power components serves to minimize mechanical stresses both in the ceramic and also in the interconnection joint between the metal and the semiconductor, the interconnection joints corresponding to brazing for mounting the semiconductor on the thermal transition layers, and thus to obtain better reliability for the electronic power modules.

In a fourth aspect of the method, the method further comprises a step of forming a radiator by additive manufacturing from the last thermomechanical transition layer of the second face of the substrate, the second face of the substrate having the second copper layer.

Forming a thermomechanical transition layer including a radiator by means of additive manufacturing makes it possible to reduce the thermal resistance of the electronic power module and to eliminate the thermal interface material that is used in the prior art. The thermal interface material is generally a thermal grease. Eliminating the thermal interface thus serves to eliminate the weak points that are associated therewith, relating in particular to its poor thermal conductivity and to it being degraded at high temperature.

This also has the consequence of enabling the electronic power module to be used at very high temperatures and at high powers.

In addition, fabricating the radiator by additive manufacturing makes it possible to fabricate radiators with complex shapes that provide effective cooling in air and that are often too complex to make using conventional technologies known for fabricating radiators.

In a fifth aspect of the method, the method further comprises a step of making a package suitable for protecting the electronic components that are to be mounted on the first face of the substrate and of making connections suitable for electrically connecting the electronic module to external electrical elements, the package and the connections being made by additive manufacturing from the last thermomechanical transition layer of the first face of the substrate, the first face of the substrate having the first copper layer.

Making the package by additive manufacturing from the last thermomechanical transition layer of the substrate enables hermetically sealed packages to be made with insulators (such as insulating gas optionally under pressure, high vacuum, insulating liquid, etc.) that are different from the insulators made with the organic materials conventionally used, such as gels or epoxy.

In addition, fabricating the metal package by 3D printing makes it possible to eliminate the polymers that are present in the prior art in the additive joint used for bonding the package, in the package, and in the silicone gel encapsulating the electronic components.

Eliminating polymers, which present poor thermal reliability at temperatures higher than 175° C., and eliminating the thermal interface material, enables the electronic power module to be used at temperatures higher than 200° C.

Electronic power modules operating in this temperature range are particularly advantageous for aviation applications, since they enable control electronics to be moved closer to heat sources, e.g. such as brakes or engines, thereby obtaining systems that are more integrated and thus making it possible to save on volume.

The increase in the surrounding temperature that is made possible also enables the dimensions of the cooling system to be reduced and thus to increase the power density of the power converter.

The metal package also serves to provide the electronic power module with electromagnetic shielding, thereby reducing the effect of external electromagnetic disturbances on the electronic components of the module.

The invention also provides a substrate for an electronic power module, the substrate comprising an insulating plate presenting opposite first and second faces, with a first metal layer arranged directly on the first face of the insulating plate, and a second metal layer arranged directly on the second face of the insulating plate. The substrate comprises, on at least one of the first and second metal layers, at least one thermomechanical transition layer comprising a material presenting a coefficient of thermal expansion less than the coefficient of thermal expansion of the metal of the metal layer.

The invention also provides an electronic power module comprising a substrate presenting a first face and a second face opposite from the first face, and a radiator mounted on the second face of the substrate, the first face of the substrate being for receiving electronic components, the substrate corresponding to the substrate as defined above.

BRIEF DESCRIPTION OF THE DRAWINGS

The invention can be better understood on reading the following description given by way of non-limiting indication and with reference to the accompanying drawings, in which.

DETAILED DESCRIPTION OF EMBODIMENTS

Figure 1:
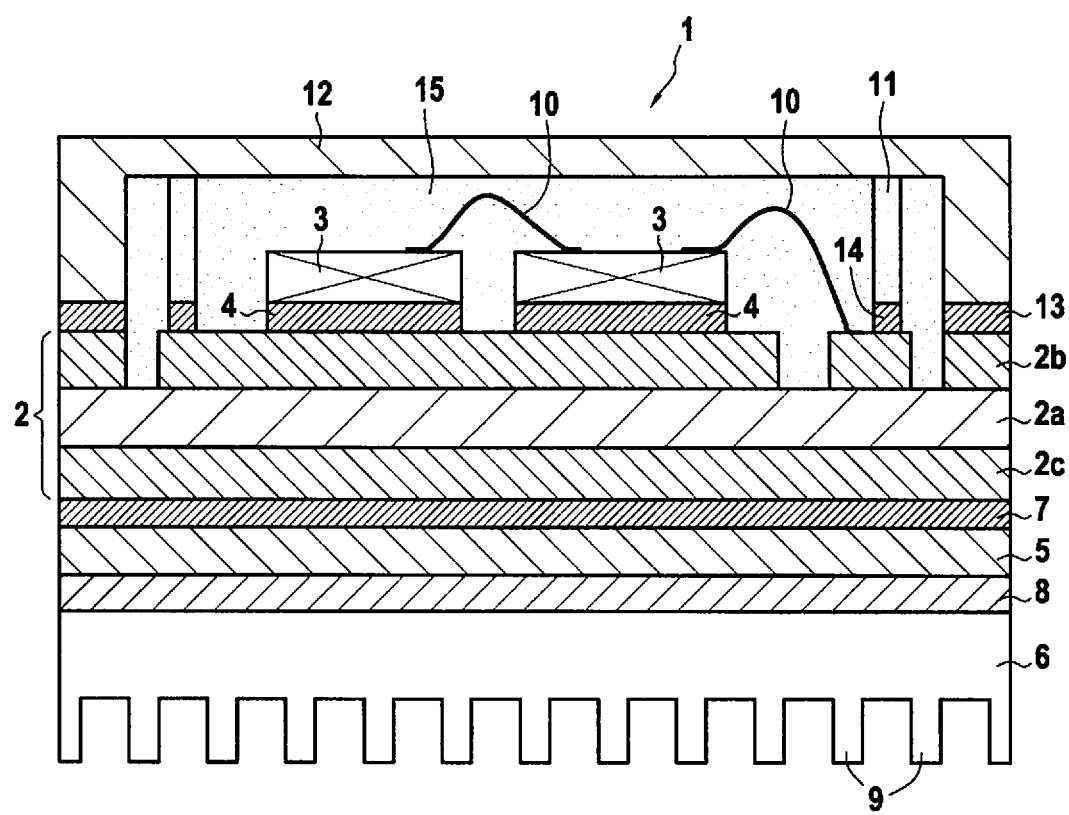
FIG. 1, described above, shows an example of an electronic power module known in the prior art.
Figure 2:
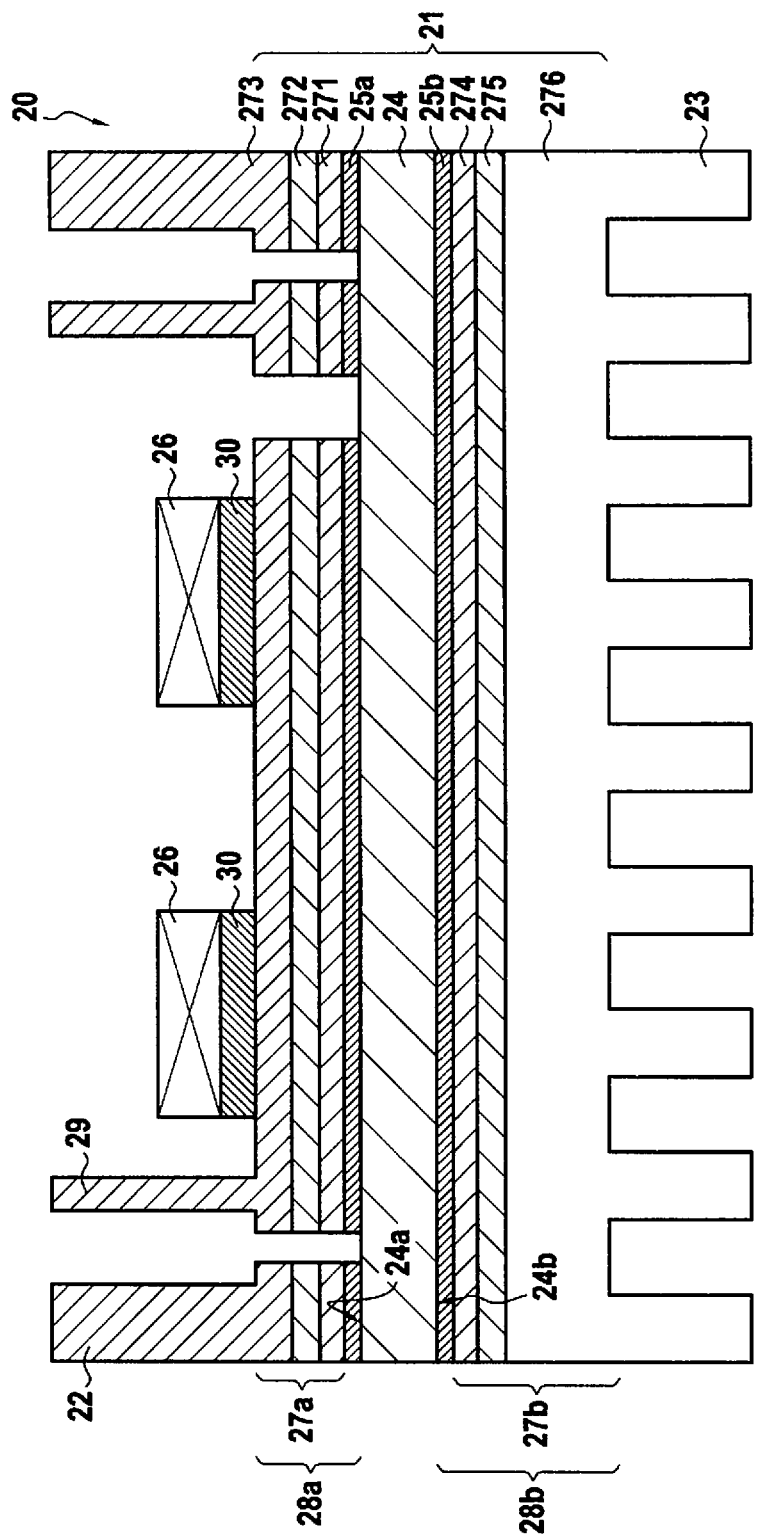
FIG. 2 is a diagram of an electronic power module in an embodiment of the invention.

FIG. 2 is a diagram of an electronic power module 20 in an embodiment of the invention.

The electronic power module 20 comprises a substrate 21, a package 22, and a radiator 23.

The substrate 21 comprises an insulating plate 24 made of ceramic, e.g. $Al_2O_3$ or AlN, presenting a first face 24a and a second face 24b opposite from the first face 24a. The insulating plate 24 also has a first copper layer 25a and a second copper layer 25b deposited by silkscreen printing, respectively on the first face 24a and on the second face 24b of the insulating plate 24, which copper layers have been subjected to annealing. The first copper layer 25a forms electrically conductive tracks for connecting to electronic components 26, and the second copper layer 25b forms thermally conductive tracks for thermally coupling to the radiator 23.

The substrate 21 also has a first lay-up 27a of thermomechanical transition layers and a second lay-up 27b of thermomechanical transition layers.

The first lay-up 27a is arranged on the first copper layer 25a. In the embodiment shown, it comprises three thermomechanical transition layers given references 271 to 273, each thermomechanical transition layer 271 to 273 being formed by additive manufacturing using an electrically conductive material that presents a coefficient of thermal expansion (CTE) that is less than that of copper, where the CTE of copper is generally about 17 ppm/° C.

In the embodiment shown in FIG. 2, the first thermomechanical transition layer 271 of the first lay-up 27a presents a CTE of about 13 ppm/° C., the second thermomechanical transition layer 272 presents a CTE of about 10 ppm/° C., and the third thermomechanical transition layer 273 presents a CTE of about 7 ppm/° C. The first thermomechanical transition layer 271 of the first lay-up 27a lies between the first copper layer 25a and the second thermomechanical transition layer 272, and the second thermomechanical transition layer 272 lies between the first thermomechanical transition layer 271 and the third thermomechanical transition layer 273.

The first copper layer 25a and the first lay-up 27a thus together form a first stack 28a presenting a CTE gradient, with CTE decreasing with increasing distance of the layer from the first face 24a of the insulating face 24 of ceramic.

The second lay-up 27b is arranged on the second copper layer 25b. In the embodiment shown, it comprises three thermomechanical transition layers referenced 274 to 276, each thermomechanical transition layer 274 to 276 being made by additive manufacturing using a thermally conductive material presenting a CTE that is less than the CTE of copper.

In the embodiment shown in FIG. 2, the first thermomechanical transition layer 274 of the second lay-up 27b presents a CTE of about 13 ppm/° C., the second thermomechanical transition layer 275 presents a CTE of about 10 ppm/° C., and the third thermomechanical transition layer 276 presents a CTE of about 7 ppm/° C. The first thermomechanical transition layer 274 of the second lay-up 27b lies between the second copper layer 25b and the second thermomechanical transition layer 275, and the second thermomechanical transition layer 275 lies between the first thermomechanical transition layer 274 and the third thermomechanical transition layer 276.

The second copper layer 25b and the second lay-up 27b thus together form a second stack 28b presenting a CTE gradient, with CTE decreasing as a function of the distance of the lay-up away from the second face 24b of the insulating plate 24 made of ceramic.

The substrate 21 comprises the insulating plate 24 made of ceramic, the first stack 28a, and the second stack 28b. In each of the stacks 28a and 28b, the CTE varies within the stack, in the embodiment shown, from 17 ppm/° C. for the copper layer 25a or 25b to a CTE greater than or equal to 3 ppm/° C. to 4 ppm/° C. in order to come close to the CTE of the insulating plate 24 made of ceramic, which presents a CTE of 7 ppm/° C. or to come close to the CTE of the semiconductor electronic components 26, which may present a CTE of about 3 ppm/° C. to 4 ppm/° C.

The CTE gradient presented by the first and second stacks 28a and 28b of the substrate serves to improve the reliability of the substrate and to offer little curving variation as a function of temperature with thick metallization layers.

In the embodiment shown in FIG. 2, the radiator 23 of the electronic power module 20 is made from the third thermomechanical transition layer 276 of the second lay-up 27b.

Thus, the second stack 28b includes the radiator and is made entirely by additive manufacturing, and it presents a CTE gradient such that its CTE decreases gradually from the second copper layer 25b to the radiator 23.

In similar manner, the package 22 of the electronic power module 20 is made from the third thermomechanical transition layer 273 of the first lay-up 27a. The package 22 serves to encapsulate hermetically the electronic components 26 mounted on the third thermomechanical transition layer 273 of the first lay-up 27a.

Thus, the first stack 28a comprises the package 22 and is made entirely by additive manufacturing, and it presents a CTE gradient with its CTE decreasing gradually from the first copper layer 25a to the package 22.

The electronic power module 20 also has connections 29 enabling the electronic power module 20 to be connected to external electrical elements that are not shown. The connections 29 are likewise made from the third thermomechanical transition layer 273 of the first lay-up 27a.

For reasons of simplification and clarity in FIG. 2, the portion forming the cover of the package 22 is not shown, but it can likewise be made by additive manufacturing, given that it is an integral portion of the package 22, or else it can be made separately and attached to the package afterwards.

In the embodiment shown in FIG. 2, the electronic components 26, and in particular the semiconductor components, are fastened and connected to the third thermomechanical transition layer 273 of the first lay-up by brazing 30.

Figure 3:
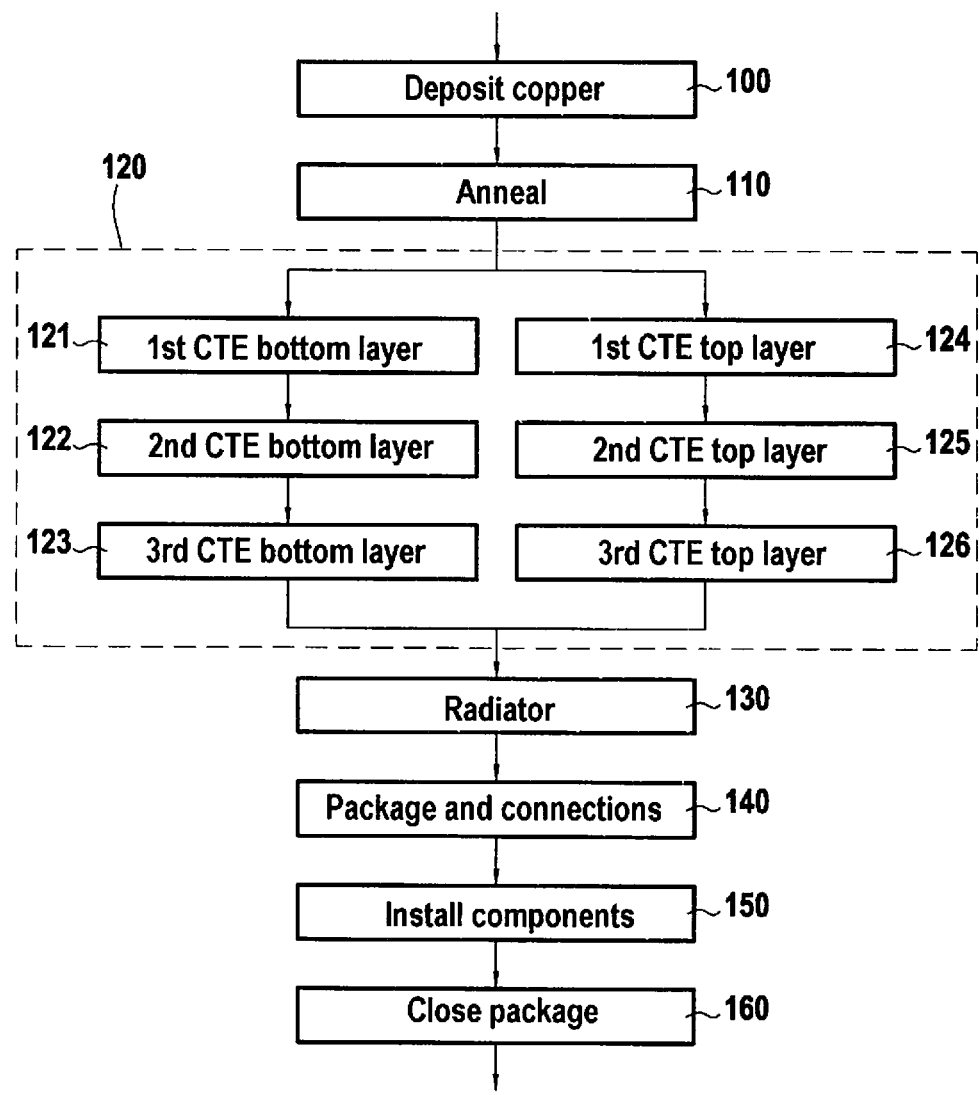
FIG. 3 is a flow chart of a method of fabricating an electronic power module in an implementation of the invention.

FIG. 3 shows a flow chart of an implementation of a method of the invention for fabricating the electronic power module 20 shown in FIG. 2.

In a first step 100 of the method, respective layers of a copper paste that is compatible with the ceramic of the plate 24 are deposited on the first and second faces 24a and 24b of the ceramic insulating plate 24 by silkscreen printing, which layers are thin, typically presenting thickness in the range 20 µm to 50 µm, the second face 24b corresponding to the bottom face in FIG. 2, and the first face 24a corresponding to the top face in FIG. 2. On the first face 24a, the copper paste is deposited with the patterns intended for electric tracks, whereas on the second face 24b, the copper paste is deposited as a solid plate, i.e. covering the entire bottom face 24b of the insulating plate 24, with the bottom face 24b being for cooling the electronic module 20.

By way of example, the copper pastes may be industrial pastes of the Heraeus or C7720 type that are compatible with a ceramic plate made of $Al_2O_3$, or else pastes of C7403 or C7404 type, which are compatible with an AlN ceramic.

In variants, the method may also include using other techniques for depositing thin metal layers from pastes or inks, such as techniques known as direct writing processes (inkjet processes, extrusion based processes, aerosol based processes, . . . ).

In a following step 110, the first and second layers of copper paste 25a and 25b are then annealed at a temperature of about 700° C. in order to eliminate solvents and other organic materials and in order to sinter the copper particles.

The first and second copper layers 25a and 25b that are obtained after annealing provide good adhesion with the ceramic of the insulating plate 24 and they bond well with the thermomechanical transition layer, respectively 271 or 274, that is to be agglomerated on the corresponding copper layer 25a and 25b by local heating produced by a laser or by an electron beam, for example.

In a following step 120 of the method, a step is performed of making the thermomechanical transition layers 271 to 276 on the copper layers 25a and 25b.

For the bottom face of the electronic power module 20 made starting from the bottom face 24b of the insulating plate 24, the powder beds of materials having CTEs in the range 7 ppm/° C. to 17 ppm/° C. are deposited on the second copper layer 25b and they are then set successively by scanning with the power source in an inert atmosphere, e.g. an argon atmosphere, over the entire surface so as to obtain a surface that is plane.

More precisely, in a first step 121 of forming thermomechanical transition layers, a first thermomechanical transition layer 274 of the second lay-up 27b is formed on the second copper layer 25b by depositing a powder bed of a material presenting a CTE of 13 ppm/° C. over the entire surface of the second copper layer 25b, and then the first thermomechanical transition layer 274 of the second lay-up 27b is set by scanning the entire surface of the bottom face 24b of the ceramic plate 24 in an inert atmosphere, e.g. by means of a laser.

In a second step 122 of forming thermomechanical transition layers, a second thermomechanical transition layer 275 of the second lay-up 27b is formed on the first thermomechanical transition layer 274 by depositing a powder bed of a material presenting a CTE of 10 ppm/° C. over the entire surface of the first thermomechanical transition layer 274, and then the second thermomechanical transition layer 275 of the second lay-up 27b is set by scanning the entire surface of the bottom face 24b of the ceramic plate 24 in an inert atmosphere, e.g. by means of a laser.

In a third step 123 of forming thermomechanical transition layers, a third thermomechanical transition layer 276 of the second lay-up 27b is formed on the second thermomechanical transition layer 275 by depositing a powder bed of a material presenting a CTE of 7 ppm/° C. over the entire surface of the second thermomechanical transition layer 275, and then the third thermomechanical transition layer 276 of the second lay-up 27b is set by scanning the entire surface of the bottom face 24b of the ceramic plate 24 in an inert atmosphere, e.g. by means of a laser.

For the top face of the electronic power module 20 made starting from the top face 24a of the insulating plate 24, the same steps are performed as for the bottom face, except that the scanning by the power source does not cover the entire surface, given that the first copper layer 25a does not cover the entire surface, but forms electrically conductive tracks on the top face of the insulating plate 24.

More precisely, in a fourth step 124 of forming thermomechanical transition layers, a first thermomechanical transition layer 271 of the first lay-up 27a is formed on the first copper layer 25a by depositing a powder bed of a material presenting a CTE of 13 ppm/° C. solely on the tracks formed by the first copper layer 25a, and then the first thermomechanical transition layer 271 of the first lay-up 27a is set by scanning the tracks formed in this way in an inert atmosphere, e.g. by means of a laser.

In a fifth step 125 of forming thermomechanical transition layers, a second thermomechanical transition layer 272 of the first lay-up 27a is formed on the first thermomechanical transition layer 271 by depositing a powder bed of a material presenting a CTE of 10 ppm/° C. solely on the tracks formed by the first thermomechanical transition layer 271 and the first copper layer 25a, and then the second thermomechanical transition layer 272 of the first lay-up 27a is set by scanning the tracks as formed in this way in an inert atmosphere, e.g. by means of a laser.

In a sixth step 126 of forming thermomechanical transition layers, a third thermomechanical transition layer 273 of the first lay-up 27a is formed on the second thermomechanical transition layer 272 by depositing a powder bed of a material presenting a CTE of 7 ppm/° C. solely on the tracks formed by the second thermomechanical transition layer 272, the first thermomechanical transition layer 271, and the first copper layer 25a, and then the third thermomechanical transition layer 273 of the first lay-up 27a is set by scanning the tracks as formed in this way in an inert atmosphere, e.g. by means of a laser.

The top last layer of the first lay-up 27a, i.e. the third thermomechanical transition layer 273, preferably presents a CTE that is as close as possible to the CTE of the semiconductor components 26 that are generally brazed on this layer, i.e. a CTE of about 3 ppm/° C. to 4 ppm/° C.

If this last layer 273 is very rough, a polishing step may be performed in order to achieve the necessary roughness.

In variants, the method may also include depositing on the top, last layer 273 finishes of the kind conventionally used in electronic assembly, of the following types: electroless nickel immersion gold (ENIG), electroless nickel electroless palladium immersion gold (ENEPIG), electroless palladium and immersion gold plating (EPIG), immersion silver and immersion gold plating (ISIG), etc., in order to avoid oxidation during brazing of the semiconductor power components 26 and in order to have compatibility with the technologies and component attachment processes that are conventionally used.

In order to form the thermomechanical transition layers, it is also possible to envisage spraying powder instead of depositing powder beds.

Variation in the CTEs of the layers is provided by varying the concentrations of the powders or the fibers of low CTE material (W, Mo, Invar, Kovar, diamond, SiC, carbon fiber, . . . ) in materials of high CTE (Cu).

The powder materials used for the thermomechanical transition layers may for example be selected from the following lists: W50Cu50, W60Cu40, W70Cu30, W80Cu20, W90Cu10, Mo50Cu50, Mo60Cu40, Mo70Cu30, Mo80Cu20, Mo85Cu15.

The power of the heat source must be sufficient to melt at least one of the materials in the mixture in order to ensure that the particles are well incorporated in a metal matrix. Among the materials mentioned above, copper presents the lowest melting temperature, and it is therefore necessary to deliver power for a time that makes it possible to reach the melting temperature of Cu, which is 1085° C.

The thickness of each copper layer or of each thermomechanical transition layer that is deposited lies in the range 20 μm to 150 μm and the CTE comes close to that of the ceramic on going away from the interface with the ceramic insulating plate 24. This makes it possible to reduce the mechanical stresses to which the ceramic of the insulating plate 24 is subjected during temperature variations, and to distribute the stresses among the various layers without having excessive stresses between two successive metal layers, which could lead to the assembly failing.

While fabricating the bottom face, the fabrication method further comprises printing continuous layers until a radiator 23 has been fabricated with various complex shapes that are effective for cooling in air, such as for example fins, pins, lattices, etc., or channels for cooling by means of a liquid.

More precisely, in a step 130 of the method a radiator 23 is formed from the third thermomechanical transition layer 276 of the second lay-up so that the lay-up includes the radiator 23, which may coincide with the third step 123 of forming thermomechanical transition layers in which the third thermomechanical transition layer 276 of the second lay-up 27b is formed;

The method of fabricating the electronic power module 20 thus makes it possible to reduce the thermal resistance of the module 20 by eliminating the thermal interface material, and it enables a radiator 23 to be fabricated having complex shapes that are very difficult to make using conventional techniques.

Likewise, for the top face, the third thermomechanical transition layer 273 of the first lay-up 27a is deposited so as to make the connections 29 and the package 22 by 3D printing in a step 140 that may coincide with the sixth step 126 of forming thermomechanical transition layers.

In order to finish off the electronic power module 20, in a step 150, the semiconductor power components 26 are then fitted on the last layer 273 of the first lay-up 27a by any of the techniques that are used conventionally, such as brazing, adhesive bonding, or sintering, for example, and then they are electrically connected, e.g. by wiring, by metal frame brazing, or by any other interconnection technique.

Finally, in a step 160, the electronic module 20 is encapsulated, i.e. filled with a silicone gel, epoxy, or an insulating liquid or gas if closure is hermetic and the package 22 is closed by additive manufacturing using the same material as the material used for the third thermomechanical transition layer 273 of the first lay-up 27a. Around the exiting connections 29 and in order to provide electrical insulation for the package between the connections and the package, it is possible to make an insulating joint out of glass or of ceramic.

The portion constituting the closure of the package may be made separately and attached to the package subsequently, by brazing, sintering, or some other assembly technique.

The invention claimed is:

1. A substrate for an electronic power module, the substrate comprising an electrically insulating plate presenting opposite first and second faces, with a first metal layer arranged directly on the first face of the insulating plate and a second metal layer arranged directly on the second face of the insulating plate; wherein the substrate comprises, on at least one of the first and second metal layers, at least one thermomechanical transition layer comprising a material presenting a coefficient of thermal expansion less than the coefficient of thermal expansion of the metal of the at least one of the first and second metal layer, and at least one stack of a metal layer and a plurality of thermomechanical transition layers, said at least one stack presenting a gradient in its coefficient of thermal expansion that decreases with increasing distance of a layer of said at least one stack from said substrate.

2. The substrate according to claim 1, wherein the coefficients of thermal expansion of the materials used for the plurality of thermomechanical transition layers lie in the range 3 ppm/° C. to 17 ppm/° C.

3. An electronic power module comprising a substrate presenting a first face and a second face opposite from the first face, and a radiator mounted on the second face of the substrate, the first face of the substrate being for receiving electronic components, wherein the substrate is a substrate according to claim 1.

4. The electronic power module according to claim 3, wherein the radiator comprises a last thermomechanical transition layer on the second face of the electrically insulating plate, the radiator being made by additive manufacturing from the last thermomechanical transition layer on the second face of the electrically insulating plate.

5. The electronic power module according to claim 3, further comprising a package suitable for protecting the electronic components mounted on the first face of the substrate, the package being made by additive manufacturing from the last thermomechanical transition layer on the first face of the electrically insulating plate.

* * * * *